(12) United States Patent
Higashiyama et al.

(10) Patent No.: US 10,596,283 B2
(45) Date of Patent: Mar. 24, 2020

(54) STERILIZATION APPARATUS

(71) Applicants: SUNTORY HOLDINGS LIMITED, Osaka (JP); PLASMATREAT GMBH, Steinhagen (DE)

(72) Inventors: Kenichi Higashiyama, Kyoto (JP); Kenta Tominaga, Kyoto (JP); Yuji Hirayama, Kyoto (JP); Kazuki Yoshihara, Kyoto (JP); Christian Buske, Steinhagen (DE); Daniel Hasse, Steinhagen (DE)

(73) Assignees: SUNTORY HOLDINGS LIMITED, Osaka (JP); PLASMATREAT GMBH, Steinhagen (DE)

( * ) Notice: Subject to any disclaimer, the term of this patent is extended or adjusted under 35 U.S.C. 154(b) by 15 days.

(21) Appl. No.: 15/767,430

(22) PCT Filed: Oct. 13, 2015

(86) PCT No.: PCT/JP2015/079391
§ 371 (c)(1),
(2) Date: Apr. 11, 2018

(87) PCT Pub. No.: WO2017/064819
PCT Pub. Date: Apr. 20, 2017

(65) Prior Publication Data
US 2018/0296714 A1   Oct. 18, 2018

(51) Int. Cl.
*A61L 2/14* (2006.01)
*A23L 3/26* (2006.01)
(Continued)

(52) U.S. Cl.
CPC .................. *A61L 2/14* (2013.01); *A23L 3/26* (2013.01); *A61L 2/202* (2013.01);
(Continued)

(58) Field of Classification Search
CPC ............... A61L 2/14; A61L 2/202; A23L 3/26
See application file for complete search history.

(56) References Cited

U.S. PATENT DOCUMENTS 5,603,895 A   2/1997 Martens et al.
5,753,196 A   5/1998 Martens et al.
(Continued)

FOREIGN PATENT DOCUMENTS

| JP | 2008-261547 | 10/2008 |
| JP | 2009-519799 | 5/2009 |
| JP | 2012-163245 | 8/2012 |

OTHER PUBLICATIONS

International Search Report issued in PCT/JP2015/079391, dated Apr. 5, 2016.

*Primary Examiner* — Sean E Conley
(74) *Attorney, Agent, or Firm* — Greenblum & Bernstein, P.L.C.

(57) ABSTRACT

A sterilization apparatus characterized in that the sterilization apparatus comprises a reactive oxygen species irradiation unit for irradiating a reactive oxygen species-containing gas which is a reaction product of plasma generated using an alternating current and a water-containing gas containing steam, the sterilization apparatus further containing an inlet unit for steam flow for supplying the water-containing gas heated to a temperature of from 50° to 300° C., wherein the reactive oxygen species-containing gas contains water in an amount equal to or greater than the amount of saturated steam. The sterilization apparatus of the present invention shows excellent sterilization activity, so that it can be suitably used in sterilization of containers for foodstuff, bottle caps sealing the openings of the containers, medical devices, foodstuff such as vegetables and meat, and the like.

6 Claims, 1 Drawing Sheet

(51) Int. Cl.
 *A61L 2/20* (2006.01)
 *A23L 3/3409* (2006.01)
(52) U.S. Cl.
 CPC ........ *A23L 3/34095* (2013.01); *A61L 2202/11* (2013.01); *A61L 2202/23* (2013.01)

(56) References Cited

U.S. PATENT DOCUMENTS

| | | |
|---|---|---|
| 2010/0021340 A1 | 1/2010 | Buske et al. |
| 2011/0008025 A1 | 1/2011 | Lee |
| 2012/0064016 A1 | 3/2012 | Lloyd et al. |
| 2013/0142694 A1 | 6/2013 | Krohmann et al. |

# STERILIZATION APPARATUS

TECHNICAL FIELD

The present invention relates to a sterilization apparatus. More particularly, the present invention relates to an apparatus of irradiating reactive oxygen species produced by plasma generated by discharge to carry out sterilization treatment, and a sterilization method using the apparatus.

BACKGROUND ART

Containers for foods or beverages (foodstuff) are required to be sterilized on inner and outer surfaces thereof. As a conventional sterilization method, a method using an aqueous hydrogen peroxide or a chemical has been known. However, there are some disadvantages that the aqueous hydrogen peroxide or chemical is likely to remain, so that the development of substitute techniques has been studied.

For example, Patent Publication 1 discloses a method including generating a plasma jet using discharge in a fluid, contacting a surface to be treated with the plasma jet, and carrying out sterilization (disinfection) by way of energy transfer from the plasma jet to the surfaces. The plasma jet as used herein is generated by air discharge in a process gas containing oxygen, preferably the air.

In addition, Patent Publication 2 discloses a method of carrying out deodorization sterilization in a refrigerator using a plasma device that generates plasma to produce ozone or reactive species. More specifically, sterilization of the deposited bacteria is carried out by generating plasma in the gap of the set electrodes to deodorize, and releasing ozone or reactive species produced in the plasma by ventilation.

RELATED ART REFERENCES

Patent Publications

Patent Publication 1: Japanese Unexamined Patent Publication No. 2009-519799
Patent Publication 2: Japanese Patent Laid-Open No. 2012-163245

SUMMARY OF THE INVENTION

Problems to be Solved by the Invention

In general, a reactive oxygen species (ROS) such as super oxide radical ($.O_2^-$), hydrogen peroxide ($H_2O_2$), or hydroxy radical (HO.) exhibits an excellent sterilizing action due to its strong oxidizing action, and these reactive oxygen species are produced mainly from oxygen molecules or water in the air. Specifically, the hydroxy radical is obtained by a reaction of a water molecule with plasma.

On the other hand, in the sterilization method of Patent Publication 1, the patent publication merely discloses a method of mixing a disinfectant substance in the process gas of the source at which plasma jet is generated in order to enhance the effects (see, [0025] of Patent Publication 1). In addition, even in the apparatus of Patent Publication 2, the amount of the reactive species produced is increased by increasing an area of the fluid contacting with the plasma (see [0037] of Patent Publication 2). It is unclear, for example, what conditions are preferred for water (steam) used in the production of reactive oxygen species as disinfectant substances, and further techniques have been demanded.

An object of the present invention is to provide a sterilization apparatus having excellent sterilizing effects and a sterilization method using the apparatus.

Means to Solve the Problems

Since radicals have shorter lives when temperatures are high, it has been known to be possible to maintain the effects of the radicals by keeping the temperature low. However, as a result of trying to produce a larger amount of the reactive oxygen species using the plasma generating apparatus, the present inventors surprisingly have found that sterilization actions are remarkably increased by supplying a water-containing gas to be supplied to a plasma generating apparatus through a pipe heated to a specified temperature so that a water content in an irradiated jet stream is equal to or greater than the amount of saturated steam. The present invention has been perfected thereby.

Specifically, the present invention relates to [1] and [2]:
[1] a sterilization apparatus characterized in that the sterilization apparatus comprises a reactive oxygen species irradiation unit for irradiating a reactive oxygen species-containing gas which is a reaction product of plasma generated using an alternating current and a water-containing gas containing steam, the sterilization apparatus further containing an inlet unit for steam flow for supplying the water-containing gas heated to a temperature of from 50° to 300° C., wherein the reactive oxygen species-containing gas contains water in an amount equal to or greater than the amount of saturated steam; and
[2] a sterilization method characterized in that the sterilization method comprises irradiating a reactive oxygen species-containing gas which is a reaction product of plasma generated using an alternating current and a water-containing gas containing steam, heated to a temperature of from 50° to 300° C., wherein the reactive oxygen species-containing gas contains water in an amount equal to or greater than the amount of saturated steam.

Effects of the Invention

The sterilization apparatus of the present invention exhibits some excellent effects that the sterilizing effects are excellent. Also, a chemical or the like which has been used in conventional sterilization does not remain because the sterilization is carried out with a fluid, which leads to simplifications of processing steps, whereby productivity can be remarkably improved.

MODES FOR CARRYING OUT THE INVENTION

The sterilization apparatus of the present invention is characterized in that when a reactive oxygen species containing hydroxy radicals is irradiated to sterilize, a water-containing gas to be mixed and reacted with plasma is allowed to flow through a pipe heated at a specified temperature in order to retain as much water by irradiated gas stream, so that the water content in the irradiated gas stream is equal to or greater than the amount of saturated steam. The reasons why the sterilizing effects are increased by heating and allowing a water-containing gas to flow through the pipe so that the irradiated gas stream has a specified water content are not unconditionally explained, but it is assumed to be as follows. Generally, since an amount of saturated steam increases if a temperature of the gas is elevated, more amounts of water can be retained as compared to that before heating by increasing the temperature of the water-containing gas. If such a high-water content gas is mixed with a gas containing plasma, the water content of the irradiated gas stream can be increased, so that the probability of allowing the plasma to react with water molecules increases, whereby consequently increasing the amount of reactive oxygen species produced, and the effects are far more advantageous even with the counter effects of shortening life of reactive oxygen species due to high temperatures. However, these assumptions do not limit the present invention thereto. Here, in the present invention, the term "sterile" or "sterilization" means breaking of live bodies of microbes or removal thereof from surfaces to be sterilized, which, for example, includes disinfection, sterilization or sterile filtration.

The sterilization apparatus of the present invention will be described more specifically based on FIG. 1 hereinbelow. Here, the sterilization apparatus shown in FIG. 1 is merely one embodiment of the present invention, without intending to limit the scope of the present invention thereto.

Figure 1:
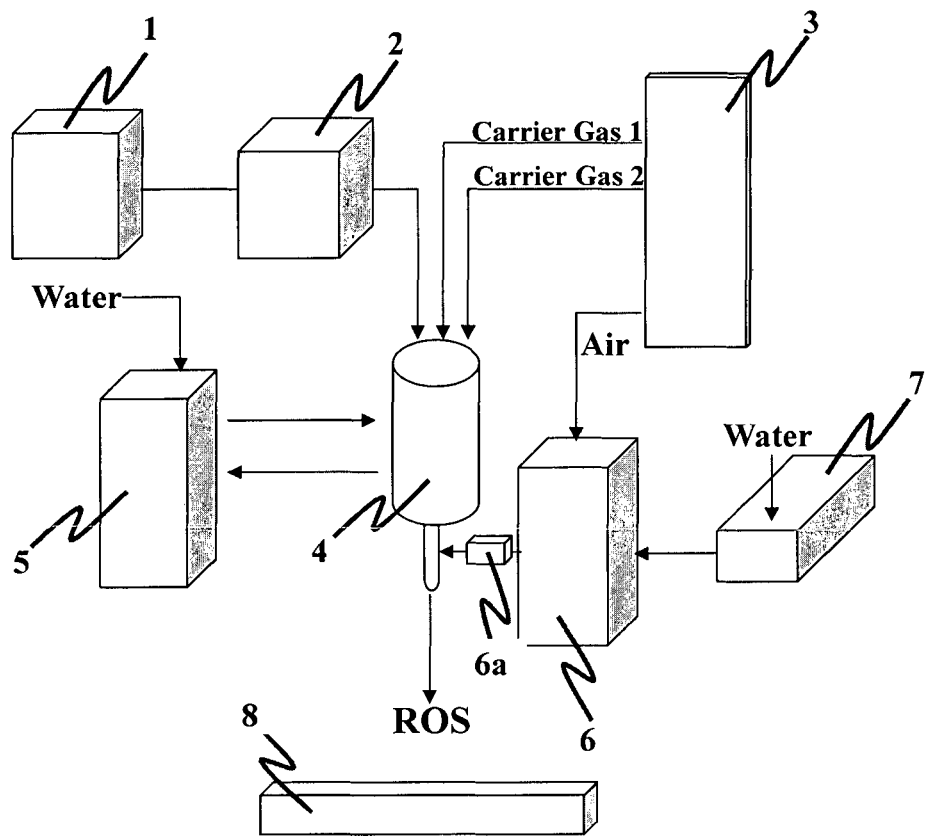
FIG. 1 is a view showing one embodiment of a sterilization apparatus of the present invention.

As shown in FIG. 1, the sterilization apparatus of the present invention comprises an inlet unit 1 for alternating current (generator unit); a high-voltage unit 2 (transformer unit); an inlet unit 3 for gas flow (control panel); a nozzle unit 4; a chiller unit 5 of the nozzle unit; an inlet unit 6 for steam flow (evaporator unit) to the nozzle unit; a heater 6a, and an inlet unit 7 for water flow (pump unit) to the evaporator unit.

The generator unit 1 is a source of generating electric charges of plasma discharge. The alternating current to be supplied is not particularly limited, and the alternating current includes, for example, ones generated at a frequency of from 10 to 15 kHz, and a voltage of from 200 to 500 V, which can be properly adjusted in accordance with known techniques. The level of amperes of the alternating current is not particularly limited, and the level can be properly adjusted depending upon the specifications of the generator unit; for example, an alternating current of 11 A may be used. Here, in the present invention, a direct current can be used in place of the alternating current, but the alternating current is preferred, from the viewpoint of adjusting voltage.

The transformer unit 2 is a device which is connected with the generator unit 1, and increases voltage of the alternating current supplied from the unit 1. As the transformer unit, any of devices that are capable of increasing voltages can be used without particular problems. In addition, the transformer unit may be integrated with the generator unit 1. The increased voltage is not particularly limited, and may be, for example, from 10 to 30 kV or so.

The control panel 3 is an device for controlling gas flows of various gases to each of a nozzle unit 4 and an evaporator unit 6, and a known control panel can be used.

Specifically, a carrier gas for generating plasma is supplied to a nozzle unit 4. As the carrier gas, the air, oxygen, nitrogen, argon, helium, and mixtures thereof can be used, among which it is preferable to use two kinds of the air and oxygen. The amount of the carrier gas supplied is not unconditionally set and depends upon the size, shape, or the like of the nozzle unit 4. For example, an embodiment includes allowing the air to flow at a rate of 6 L/min, and oxygen to flow at a rate of 3 L/min.

The air for mixing to the steam needed for producing reactive oxygen species from plasma is introduced to the evaporator unit 6. By using a water-containing gas in which the steam is mixed with the air, the mixing of the plasma and steam is accelerated, whereby hydroxy radicals can be efficiently produced from the steam. The amount of the air introduced to the evaporator unit 6 is the same as the amount of the water-containing gas introduced to the nozzle unit 4. For example, an embodiment of allowing the air to flow at a rate of 3 L/min is exemplified. Here, the air as used herein refers to a gas of which relative humidity is from 0 to 10% by volume or so at 20° C.

The nozzle unit 4 is a device of irradiating reactive oxygen species obtained by generating plasma, which is also referred to as a reactive oxygen species irradiation unit. The unit comprises an internal electrode and an external electrode, and an electric field can be generated between the internal and external electrodes by applying a voltage from the transformer unit 2. In addition, the internal electrode may be connected with a coil, so that an even larger electric field can be formed. The shape, size or the like of the coil can be adjusted in accordance with the technical common knowledge of one of ordinary skill in the art.

In addition, the nozzle unit comprises a gas inlet port and a reactive oxygen species irradiation port, wherein the gas inlet port exists at an end of an opposite side to an end part of the reactive oxygen species irradiation inlet. Moreover, the gas inlet port is connected with a pipe from the control panel 3, wherein plasma is generated by allowing a carrier gas to pass through the electric field generated as mentioned above. Since the plasma produced as described above is also a fluid, the plasma may also be referred to as a plasma jet. On the other hand, the reactive oxygen species irradiation port has a tubular structure or a conical structure that is tapered toward the discharge opening, and connected with a pipe for allowing a water-containing gas to flow from the evaporator unit 6 at any of the parts before reaching the discharge opening.

The present invention is characterized by arranging a heating device (heater 6a) communicating from an evaporator unit 6 to a pipe connected to the above reactive oxygen species irradiation port. The above heater 6a may be heating the entire pipe, or partly, and in order to stably heat the water-containing gas passed therethrough, it is preferable that the entire pipe is heated. In addition, the heater 6a may be integrated with the evaporator unit 6. The heating temperature is 50° C. or higher, and preferably 100° C. or higher, and 300° C. or lower, and preferably 200° C. or lower, from the viewpoint of keeping larger amounts of water in the water-containing gas. Here, the heating temperature as used herein is a set temperature of a heater 6a. The water-containing gas heated as described above is reacted with the above plasma generated to produce reactive oxygen species, which is then irradiated from the discharge opening of the reactive oxygen species irradiation port as a reactive oxygen species-containing gas.

The nozzle unit 4 is not particularly limited in the shape or size so long as the nozzle unit comprises the above parts. For example, the nozzle unit having a structure comprising a gas inlet port arranged at an upper end of a cylindrical structure, and a reactive oxygen species irradiation port having a tubular structure having a diameter smaller than the diameter of the apparatus at a lower end thereof is exemplified. The cylindrical structure may form a layered structure, and, for example, a structure in which a coil is formed in the surroundings of the tube through which a carrier gas passes, and optionally a layer of an insulation material is further formed in the surroundings of the coil is exemplified. The tube is not particularly limited so long as the tube is an electroconductive material, and known materials in the art can be used. In addition, the insulation material is also not particularly limited, and a known insulation material in the art can be used.

The chiller unit 5 of the nozzle unit is a device for allowing a chilling water to flow to the nozzle unit 4, and a known chiller can be used. Since the nozzle unit 4 generates heat by applying a high voltage, it is preferable to chill the nozzle unit. As the chilling water, waters having a temperature of, for example, 5° C. or so are preferably used, and the chilling water may be circulated between the nozzle unit 4 and the chiller unit 5. The flow rate of the chilling Water can be properly adjusted so that the surface temperature of the nozzle unit 4 is controlled to 25° C. or lower. Here, the surface temperature of the nozzle unit 4 can be measured with a contact-type thermometer.

The evaporator unit 6 to the nozzle unit is a device of allowing a water-containing gas to flow to the nozzle unit 4, wherein the evaporator unit is connected to a reactive oxygen species irradiation port of the nozzle unit 4 as mentioned above via a pipe provided with a heater 6a. When the water-containing gas is allowed to flow, first, water from a pump unit 7 is heated with electric heating wires installed therein to produce steam, and a mixture of the steam with the air from the control panel 3 is introduced to the nozzle unit 4 as a water-containing gas. Here, the pump unit 7 may be integrated with the evaporator unit 6. The heating temperature of the electric heating wires can be properly adjusted depending upon the amount of water pumped, which is exemplified by, for example, 300° C. Also, the amount of water pumped from the pump unit 7 can be adjusted depending upon the amount of steam needed to produce reactive oxygen species. In the present invention, the amount of water pumped from the pump unit 7 is preferably 0.5 mL/min or more, and more preferably 2.0 mL/min or more. In addition, although the upper limit of the amount is not particularly set, the amount of water pumped from the pump unit 7 is preferably 6 mL/min or less, and more preferably 5 mL/min or less. The steam thus obtained is mixed with the air introduced from the control panel 3 in a volume ratio of from 0.2 to 2.5 or so, and the water-containing air is introduced to a reactive oxygen species irradiation port of the nozzle unit 4 via a pipe heated with a heater 6a mentioned above. The mixing volume ratio of steam to the air can be modified by fluctuating the amount of the water passed, and the amount of steam contained in the water-containing air can be increased by increasing the amount of the water passed. Examples of the mixing volume ratio of the plasma jet produced in the nozzle unit 4 to the water-containing gas from the evaporator unit 6 [plasma jet/water-containing gas (volume ratio)] include from 0.8 to 2.6.

In addition, the sterilization apparatus of the present invention may comprise an irradiation platform 8 on which an object to be sterilized is placed, besides the units mentioned above. The irradiation platform is not particularly limited so long as the object to be sterilized can be placed, and it is preferable that the object can be placed at a temperature preferably 50° C. or lower, and more preferably 40° C. or lower, from the viewpoint of not allowing hydroxyl radical to degrade by high temperatures.

Here, the sterilization apparatus of the present invention may further comprise other units, beside the units mentioned above. Other units are exemplified by a shielding partition for preventing diffusion of reactive oxygen species-containing gas, and the like.

Thus, the reactive oxygen species-containing gas is irradiated from the sterilization apparatus of the present invention. The irradiated reactive oxygen species-containing gas is obtained by mixing the reactive oxygen species-containing gas and a water-containing gas passing through the pipe heated to a specified temperature, so that the water content would be an amount equal to or greater than the amount of saturated steam. Assuming that a case where the saturated steam containing water has a relative humidity of 100%, the reactive oxygen species-containing gas irradiated from the sterilization apparatus of the present invention would have a relative humidity of 100% or more, and preferably show a relative humidity of 101% or more, and more preferably 102% or more. Here, even if gases have the same water content, those having higher relatively humidity would have higher reactivity with plasma; therefore, although it cannot be generalized, it is preferable that water is contained in an amount of, for example, 0.1 g/L or more, and preferably 0.15 g/L or more or so. Since the saturated steam contains a large amount of water, the amount of reactive oxygen species produced would become large, and has excellent sterilization activity. In addition, since reactive oxygen species-containing gas is a fluid, even those having three-dimensional structures can be sterilized, thereby exhibiting excellent effects that the residues do not remain at edges and corners.

The irradiated reactive oxygen species-containing gas is warm due to the discharge within the nozzle unit 4 or the water-containing gas from the evaporator unit 6 and a heater 6a, of which temperature is preferably from 55° to 80° C., and more preferably from 60° to 80° C. Because of the warmth, the heat load of the irradiated object is considered to be small. Here, the temperature of the reactive oxygen species-containing gas refers to a temperature of reactive oxygen species-containing gas at the discharge opening of the reactive oxygen species irradiation port that is measured with a thermocouple thermometer.

In addition, a temperature difference between the reactive oxygen species-containing gas and the surface of the object to be sterilized is, for example, 10° C. or more, and more preferably from 30° to 40° C., from the viewpoint of increasing a reactivity of radicals. The temperature of the surface of the object to be sterilized as used herein refers to a surface temperature of an object to be sterilized that is measured with a contact-type thermometer.

The irradiation speed can be adjusted according to the amount of the gas supplied and the shape of the reactive oxygen species irradiation port, and, for example, the irradiation speed is exemplified by 50,000 mm/sec. The irradiation time is not unconditionally set depending upon the object irradiated, and for example, an irradiation time is exemplified by from 0.05 to 1 second.

In addition, it is preferable that the distance between the reactive oxygen species irradiation port and the surface of the object to be sterilized is, for example, from 5 to 50 mm.

The sterilization apparatus of the present invention is used for irradiating reactive oxygen species to an object in need of sterilization. The object is exemplified by, for example, containers for foodstuff, bottle caps for sealing the opening part of the containers, medical devices, foodstuff such as vegetables and meat, and the like.

The present invention also provides a sterilization method characterized in that when sterilization is carried out by irradiating a reactive oxygen species generated from plasma, the water content of the gas stream containing reactive oxygen species is in an amount equal to or greater than the amount of saturated steam.

Specifically, the method is characterized by mixing plasma generated using alternating current with a water-containing gas containing steam while heating to a temperature of from 50° to 300° C., and irradiating the reactive oxygen species-containing gas containing water in an amount equal to or greater than the amount of saturated steam to an object to be sterilized. Since the gas (reactive oxygen species-containing gas) obtained by mixing plasma (for example, plasma jet stream) and a water-containing gas contains water in an amount equal to or greater than the amount of saturated steam, the probability of allowing the generated plasma to react with water molecules increases, whereby consequently, the amount of reactive oxygen species formed would be increased. In order to have water contained in an amount equal to or greater than the amount of saturated steam in the reactive oxygen species-containing gas, the water-containing gas is heated to a temperature of 50° C. or higher, and preferably 100° C. or higher, and a temperature of 300° C. or lower, and preferably 200° C. or lower, and supplied. The method of heating a water-containing gas can be carried out in accordance with a known technique. For example, an example includes an embodiment of heating a pipe for supplying a water-containing gas with a heater or the like. Here, the plasma can be generated in accordance with a known technique, and the plasma that is generated using alternating current is preferably used in the present invention.

In addition, in the above sterilization method, it is preferable that the object to be sterilized is placed so that a temperature difference between the reactive oxygen species-containing gas and the surface of the object to be sterilized is preferably 10° C. or more, and more preferably from 30° to 40° C. or so. Specifically, it is preferable that the object to be sterilized is placed on an irradiation platform of which surface temperature is preferably 50° C. or lower, and more preferably 40° C. or lower.

One embodiment of the sterilization method of the present invention includes a method using the sterilization apparatus of the present invention. The specifications of the sterilization apparatus, the method of its use and the like are as described in the section of the sterilization apparatus of the present invention. For example, the water-containing air is allowed to pass through a pipe heated at a temperature of from 50° to 300° C.

EXAMPLES

The present invention will be described more specifically by means of Examples given hereinbelow, without intending to limit the present invention thereto.

Test Example 1

The temperature for pumping a water-containing gas in the sterilization apparatus of the present invention was studied.

<Preparation of Bacterial Solution and Preparation of Bacteria-Inoculated Bottle Cap>

Figure 2:
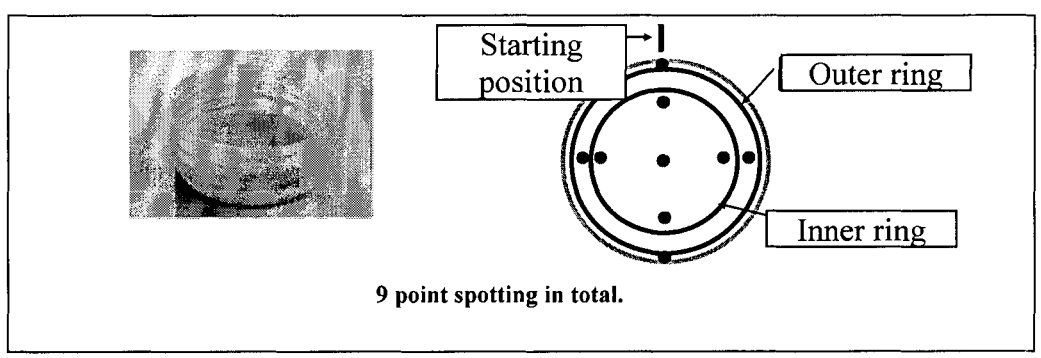
FIG. 2 is a view showing bacteria-inoculated sites in a resin bottle cap used in Examples.

Using a bacterial solution of fibroblast bacterium *Bacillus atrophaeus*, bacterial solutions of various concentrations (3 standards within the concentration range of from $2 \times 10^5$ to $2 \times 10^7$ CFU/mL) were prepared. The obtained bacterial solution was inoculated in an amount of 1 μL×9 spots for each resin bottle cap (material: polyethylene) (each concentration n=5) as shown in FIG. 2. Here, the inoculated resin bottle cap which was allowed to stand in a sterile petri dish for 24 hours to dryness was used.

<Irradiation of Reactive Oxygen Species>

Using the sterilization apparatus of the present invention shown in FIG. 1, a resin bottle cap that was inoculated was irradiated with reactive oxygen species-containing gas twice for 0.5 seconds (total of 1 second) per bottle cap from a distance 30 mm upstream side, and the irradiated bottle cap was collected on a sterile petri dish. Here, the operating conditions of the sterilization apparatus of the present invention were as follows.

(Operating Conditions of Sterilization Apparatus)
Generator unit 1 of alternating current: frequency: 14 kHz, voltage: 300 V, electric current: 11 A
Transformer unit 2: The raised voltage: 20 kV
Control panel 3: amount of air flow: 6 L/min, amount of oxygen flow: 3 L/min (hereinabove, go to nozzle unit 4), amount of air flow: 3 L/min (go to evaporator unit 6)
Nozzle unit 4: irradiation temperature of reactive oxygen species-containing gas: as listed in Table 1, irradiation speed: 50,000 mm/sec
Chiller unit 5: chilling water: 5° C.
Evaporator unit 6: electric heating wire: 300° C., amount of water-containing gas flow: 6.7 L/min (amount of plasma jet/water-containing gas flow (volume ratio)=9/6.7)
Heater 6a: pipe temperature: as listed in Table 1
Pump unit 7: amount of water pumped: as listed in Table 1
Irradiation platform 8: surface temperature: 25° C.

<Measurement of Sterilization Activity Values>

The resin bottle cap subjected to irradiation of a reactive oxygen species-containing gas was taken out of the sterile petri dish, and 5 mL of TSA liquid medium (manufactured by BD Falcon) was injected to the petri dish, and kept at 35° C., a temperature suitable for proliferation of microbes for 3 days. After the cultivation, the number of petri dishes in which media became turbid due to microbial proliferation was judged positive as a bottle cap count, and the sterilization activity value LRV (Log Reduction Value) was calculated according to the most probable number method (MPN method). The results are shown in Table 1. Here, the "D" value showing the sterilization activity is the number of bacteria per bottle cap expressed by common logarithm (LOG value), and is a value obtained by subtracting the number of bacteria after the treatment (LOG value) from the number of bacteria before the treatment (LOG value). The larger the number, the higher the sterilization activity, and the number of 4.5 D or more would show no problem as the sterilization treatment of food containers.

TABLE 1

| | | Reactive Oxygen Species-Containing Gas | | | | |
|---|---|---|---|---|---|---|
| | Pipe Temp., ° C. | Amount of Water Pumped, mL/min | Temp., ° C. | Water Content, Relative Humidity, % | Water Content, g/L | LRV, D Value |
| Comp. Ex. 1 | No Heater 35° C. | 1.2 | 51 | 94 | 0.08 | 3.4 D |
| Comp. Ex. 2 | 105° C. | 1.2 | 64 | 49 | 0.08 | 3.4 D or less |
| Ex. 1 | 105° C. | 3.0 | 64 | 105 | 0.17 | 6.3 D or more |

It can be seen from Table 1 that when the water-containing gas is allowed to pass through the pipe, in a case where the pipe is heated and the amount of steam mixed is large (Example 1), the sterilization activity is high, where in a case unheated (Comparative Example 1) or a case where the amount of steam mixed is small even while heating (Comparative Example 2), the sterilization activity is low. Here, the relative humidity, %, and the water content, g/L of the reactive oxygen species-containing gas listed in Table 1 were calculated as follows. Here, when the amount of water pumped is 1 mL/min, the volume of the steam was calculated as 1 g/min (amount of water pumped)/18 g (molecular weight of water)×22.4 L (the volume corresponding to 1 mol of the gas)=1.2 L/min, and the water content was filled in from the values obtained from the amount of saturated steam and the relative humidity. For example, in the case of Comparative Example 1, since the amount of saturated steam of the gas of which temperature is 51° C. is 0.087 g/L, the relative humidity of the reactive oxygen species-containing gas is 1.2 g/min (amount of water pumped)/[[13.5× (273+51)/(273+25) L/min] (total amount pumped of the plasma jet and the water-containing gas at 51° C.)×0.087 g/L (amount of saturated steam)]×100=94%. In addition, since the saturated steam amount when the gas temperature is 64° C. is about 0.160 g/L, for example, the relative humidity of the reactive oxygen species-containing gas of Comparative Example 2 is 1.2 g/min (amount of water pumped)/[[13.5× (273+64)/(273+25) L/min] (total amount pumped of the plasma jet and the water-containing gas)×0.160 g/L (amount of saturated steam)]×100=49%, in contrast to the relative humidity of the reactive oxygen species-containing gas of Example 1 would be calculated to be 3.0 g/min (amount of water pumped)/[[15.7 L/min×(273+64)/(273+25) L/min] (total amount pumped of the plasma jet and the water-containing gas at 64° C.)×0.160 g/L (amount of saturated steam)]×100=105%. Parts of the steam that exceeded the relative humidity of 100% are considered to be condensed. As described above, it is suggested that even if the gas stream irradiated from the reactive oxygen species irradiation port is at the same temperature, the one having a higher relative humidity in the gas stream has higher sterilization activity. In addition, excellent sterilizing effects are obtained while the reactive oxygen species was irradiated for as long as only 1 second, thereby suggesting the improvement in productivity.

INDUSTRIAL APPLICABILITY

The sterilization apparatus of the present invention shows excellent sterilization activity, so that it can be suitably used in sterilization of containers for foodstuff, bottle caps sealing the openings of the containers, medical devices, foodstuff such as vegetables and meat, and the like.

EXPLANATION OF NUMERALS 1 an inlet unit for alternating current (generator unit)
2 a high-voltage unit (transformer unit)
3 an inlet unit for gas flow (control panel)
4 a nozzle unit
5 a chiller unit
6 an inlet unit for steam flow (evaporator unit)
6a a heater
7 an inlet unit for water flow (pump unit)
8 an irradiation platform

The invention claimed is:

1. A sterilization apparatus, comprising:
a reactive oxygen species irradiator having a gas inlet port and an irradiation port for irradiating a reactive oxygen species-containing gas which is a reaction product of plasma generated using an alternating current and a water-containing gas containing steam;
an evaporator having a steam flow inlet for supplying the water-containing gas to the reactive oxygen species irradiator; and
a heater connecting the evaporator and the irradiation port of the reactive oxygen species irradiator so as to heat the water-containing gas to a temperature of from 50° to 300° C., thereby generating the reactive oxygen species-containing gas comprising water in an amount equal to or greater than the amount of saturated steam.

2. The sterilization apparatus according to claim 1, further comprising an irradiation platform on which an object to be sterilized is placed at a temperature of 50° C. or lower.

3. A sterilization method, comprising irradiating a reactive oxygen species-containing gas which is a reaction product of plasma generated using an alternating current and a water containing gas containing steam, heated to a temperature of from 50° to 300° C., wherein the reactive oxygen species-containing gas comprises water in an amount equal to or greater than the amount of saturated steam.

4. The sterilization method according to claim 3, wherein a temperature difference between the object to be sterilized and the reactive oxygen species-containing gas is 10° C. or more.

5. The sterilization method according to claim 3, using a sterilization apparatus comprising a reactive oxygen species irradiator for irradiating the reactive oxygen species-containing gas, the sterilization apparatus further comprising a steam flow inlet for supplying the water-containing gas heated to the temperature of from 50° to 300° C. to the reactive oxygen species irradiator.

6. A sterilization method using the sterilization apparatus as defined in claim 1, comprising irradiating the reactive oxygen species-containing gas which is the reaction product of the plasma generated using the alternating current and the water-containing gas containing steam.

* * * * *